United States Patent [19]

Fischell

[11] Patent Number: 4,572,168
[45] Date of Patent: Feb. 25, 1986

[54] FULLY IMPLANTABLE VAPOR PRESSURE ACTUATED PENILE ERECTION DEVICE AND METHOD

[76] Inventor: Robert E. Fischell, 1027 McCeney Ave., Silver Spring, Md. 20901

[21] Appl. No.: 563,455

[22] Filed: Dec. 20, 1983

[51] Int. Cl.$^4$ ............................................. A61F 5/00
[52] U.S. Cl. .................................... 128/79; 604/131; 604/141
[58] Field of Search ............... 128/79 A; 604/131, 141

[56] References Cited

U.S. PATENT DOCUMENTS

| | | | |
|---|---|---|---|
| 1,133,958 | 3/1915 | Henderson. | |
| 3,832,996 | 9/1974 | Kalnberg | 128/79 |
| 3,853,122 | 12/1974 | Strauch | 128/79 |
| 3,954,102 | 5/1976 | Buuck | 128/79 |
| 4,009,711 | 5/1977 | Uson | 128/79 |
| 4,151,840 | 5/1979 | Barrington | 128/79 |
| 4,235,227 | 11/1980 | Yamanaka | 128/79 |
| 4,265,241 | 5/1981 | Portner et al. | 604/141 |
| 4,267,829 | 5/1981 | Burton et al. | 128/79 |
| 4,318,396 | 5/1982 | Finney | 128/79 |
| 4,342,308 | 8/1982 | Trick | 128/79 A |
| 4,353,360 | 10/1982 | Finney et al. | 128/79 |
| 4,360,010 | 11/1982 | Finney | 128/79 A |
| 4,364,379 | 12/1982 | Finney | 128/79 |
| 4,381,767 | 5/1983 | Finney | 128/79 |
| 4,399,812 | 8/1983 | Whitehead | 128/79 |
| 4,407,278 | 10/1983 | Burton et al. | 128/79 |

OTHER PUBLICATIONS

Management of Erectile Impotence, Use of Implantabale Inflatable Prosthesis, Scott et al. Urology, Jul. 1973, vol. II, No. 1.
"Implantable Drug Dispenser," *NASA Tech. Brief,* vol. 7, No. 1, Item #36 (Fall 1982); prepared by J. J. Bobrow.

*Primary Examiner*—Curtis R. Davis
*Attorney, Agent, or Firm*—Fleit, Jacobson, Cohn & Price

[57] ABSTRACT

Disclosed is a prosthesis for implantation entirely within the corpus carvensoum of the penis. The prosthesis is vapor pressure driven and through the displacement of a working fluid effects physiologically normal erectile and flaccid states. In one general embodiment, a movable wall is driven by permitting the pressurant to expand while remaining essentially at normal body temperatures. In another embodiment, the pressurant is heated by an external source of electrical energy.

21 Claims, 12 Drawing Figures

FULLY IMPLANTABLE VAPOR PRESSURE ACTUATED PENILE ERECTION DEVICE AND METHOD

BACKGROUND OF THE INVENTION

1. Field of the Invention

This invention relates to an improved, manually actuated, hydraulic device to provide a penile erection for human males who suffer the dysfunction of erectile impotence.

2. Description of the Prior Art

The normal male achieves an erection when a multitude of small blood vessels within a long cylindrical section on each side of the penis called the corposum cavernosum fills with blood as a result of an increase in the vessels' output resistance to blood flow. There are two such parallel cylinders in the penis (the plural being the corpora cavernosa) which simultaneously become engorged with blood, thereby producing a penile erection. Unfortunately, there are 10 million men in the United States alone who are unable to achieve a penile erection.

There are many causes for impotency in the human male, both psychological and physiological. Among the physiological causes are: long term diabetes, damage to the spinal cord, multiple sclerosis, a surgical procedure in the lower abdomen that has caused nerve damage in the genital region, and advanced age. Such impotence often destroys the male's psychological well being, and often seriously disrupts or even causes the dissolutionment of an otherwise fulfilling relationship. It is therefore not surprising to find that the patent art is replete with examples of artificial penile erection devices.

One of the earliest prosthetic devices whose object was to achieve a penile erection is described by Henderson in U.S. Pat. No. 1,133,958 (March 1915). This device suggests the use of an external truss to stiffen the penis by preventing the back-flow of blood. Since the truss is removable, it is a simple matter to obtain a normal flaccid state. However, the external truss mechanism also prevents in-flow of blood and, therefore, cannot provide the five conditions required of a normally erect penis; namely, during erection the penis should become longer, thicker, harder, stiffer, and have a generally upward angle.

Kalnberz, in U.S. Pat. No. 3,832,996 (September 1974), describes two stiff rods designed to be implanted in the corpora cavernosa to attain a penile erection. Although this system provides a longer, thicker, and stiffer erectile state, it does not provide a generally upward angle, and the flaccid state is no longer achievable.

An improved rod is described by Barrington in U.S. Pat. No. 4,151,840 (May 1979), which rod provides a longer, thicker, and stiffer erectile state. Furthermore, the device can be bent downwardly by hand to achieve the flaccid condition. However, in the flaccid condition, the penis is just as long and thick as in the erectile state; also, it is unnaturally stiff and hard.

A manually actuated fluid driven system is described by Strauch et al in U.S. Pat. No. 3,853,122 (December 1974). One drawback in the Strauch et al system is that the required energy for moving the working fluid from the storage container or reservoir thereof must be obtained by manually squeezing the reservoir. A disadvantage of this design is that if the container is large enough to hold a volume sufficient to cause an appreciable change in size between the erectile and flaccid states, then it is too large to be placed in the scrotum. If the fluid container is placed in the abdomen (where it must be located just under the skin so that it can be readily manipulated), it would cause some preceptible abdominal distortion, and would certainly be distinctly felt by the man in whom it was implanted. Further, another difficulty is that fluid exits the region of the penis automatically through a metering means not under external control. The penis therefore could become flaccid too quickly, or could take an unreasonably long time to become flaccid, all depending upon the configuration of the metering means.

Buuck, in U.S. Pat. No. 3,954,102 (May 1976), describes a manually actuated, fluid driven, inflatable penile prosthesis with two cylinders in the corpora cavernosa. The Buuck prosthesis achieves the erectile goals of a longer, thicker, harder, and stiffer penis with a generally upward angle during erection, and also provides a physiologically normal flaccid state. Furthermore, the Buuck invention overcomes one shortcoming of the Stauch et al invention in that it utilizes a large reservoir but that the fluid container is placed deep inside the abdomen where it cannot be felt but where it can be operated remotely by a pump located in the scrotum. However, this device still has certain major shortcomings. For example, when the penis is in the erectile state, its upward angle may not reach that achieved in a normal male. Further, the pump and release valve are located in the scrotum, which is one of the body sites most disposed to postoperative discomfort and infection. The Buuck device requires multiple strokes of the pump within the scrotum to achieve an erection, which could require one or more minutes of pumping, especially if the patient does not have the manual dexterity required for pumping a small bulb located within the scrotum. Furthermore, the release valve in the scrotum must be held for on the order of ten to fifteen seconds to return the penis to the flaccid state. Also, a comparatively large reservoir is required by Buuck because fluid cannot be added after implant without surgical intervention. As a consequence of the large reservoir and small displacement pump used by Buuck, it is possible to permanently distend or even rupture the stiffener cylinders by excessive pumping. Additionally, because of the many separate pieces of tubing and other parts required by the Buuck device it is necessary to fill and then assemble the many separate parts during the surgical implant. This is a time consuming and therefore costly procedure and can lead to leaking and broken connections.

A further element of the prior art is U.S. Pat. No. 4,009,711 (March 1977), which issued to Uson, and which describes a non-distensible portion of a stiffener cylinder that is placed in the root of the corpus cavernosum, and a distensible portion that is located within the pendulous portion of the corpus cavernosum. Although there may be valid reasons to provide a structure such as that described by Uson, it is disadvantageous to have a considerable portion of the stiffener cylinder located within the root of the corpus cavernosum if it is not pliable and distensible. In this regard, some shortcomings of the Uson device are that the penis does not feel natural in the flaccid condition because there is a rigid object just beneath the skin at the base of the penis. Furthermore, the shape of the penis in the flaccid condition is not physiologically normal, nor is there stress relief provided for the elastomer stiffener cylinder during the flaccid state (which is most of the time) because the cylinder does not begin its downward curve while still supported within the root of the corpus cavernosum. Additionally, a greater extended length of the penis in the erectile state cannot be achieved because the cylinder does not begin its extendible portion within the root of the corpus cavernosum.

All of the three patents as described immediately above, namely Strauch et al (U.S. Pat. No. 3,853,122), Buuck (U.S. Pat. No. 3,954,102) and Uson (U.S. Pat. No. 4,009,711), require equipment to be located outside of the corpora cavernosa; this is a disadvantage, because the more extensive is the surgery and the number of devices within the human body, the greater is the risk of infection and the possibility that some interconnecting tubing will become detached, broken or twisted closed. Ideally, surgery would be limited to only the penis. Because others are aware of this desire for a minimal implant, there is additional prior art that describes devices requiring the implantation to be only within the penis while trying to obtain more physiologically normal erectile and flaccid states.

In one embodiment of an invention by Burton, U.S. Pat. No. 4,267,829 (May 1981), FIGS. 5 and 6 show a penile erection device which has no portion of the system outside of the corpus cavernosum. The Burton invention obtains rigidity by diminishing the diameter of a front section of the penile implant while stiffening a rear portion of the pendulous section of the implanted cylinders. An advantage of this design is that no part of the device is outside of the pendulous penis and its root. A significant disadvantage of the Burton design, as shown in FIG. 5 of the patent, is that when the erectile state is desired, most of the pendulous portion of the penis is, in fact, reduced in diameter which is entirely contrary to that which is physiologically normal.

In U.S. Pat. No. 4,318,396 by Finney (March 1982), a specific embodiment shown in FIGS. 10 and 11 (flaccid and erectile states, respectively), again illustrates a penile erection device entirely contained within the corpus cavernosum. In this design, fluid is pushed from a rear section of the pendulous portion (but not the root) into the front portion, therefore making the penis rigid. A disadvantage of this design is that the pendulous portion decreases in length during erection which again is entirely contrary to normal physiology.

Another patent by Finney, U.S. Pat. No. 4,353,360 (October 1982), again shows a device entirely implanted within the corpus cavernosum. This invention shows fluid from an outer flexible cylinder being pumped into an inner cylinder by manually pumping at the base of the pendulous portion of the penis. Again this design has the disadvantage that the erectile state is obtained by removing fluid from the outer cylinder of the implant, thus decreasing the diameter of the penis during erection as compared to its diameter in the flaccid state. Again this is contrary to normal physiology.

Still another invention by Finney, U.S. Pat. No. 4,364,379 (December 1982), once more teaches a device implanted entirely within the corpus cavernosum. In this case fluid is pumped from the base portion of the pendulous section of the device into the tip portion. This again is contrary to normal physiology, because in the erectile state, the diameter of the penis at its base where it joins the body is reduced, rather than increased. Furthermore, the decreased base diameter reduces the stiffness of the prothesis at its most vital point. Therefore the erectile state may not maintain a normal upward angle during sexual activity.

Another element of the prior art is U.S. Pat. No. 4,399,812 by Whitehead (August 1983). Again in this design stiffness during the erectile state is obtained by pumping fluid from the rear part of the pendulous portion of the penis into the front portion. The Whitehead design is again contrary to normal physiology because it shortens the penis during the erectile state which is undesirable.

The last of the inventions described in issued patents to be discussed herein in U.S. Pat. No. 4,407,278 (October 1983) by Burton et al. The design described by Burton et al is again a means of manually pumping fluid from one portion of a cylinder contained within the corpus cavernosum to the distal portion of that cylinder contained in the pendulous portion of the penis. In this case the fluid is manually pumped from a root portion of the cylinder. The Burton et al invention still requires manual pumping and from a particularly awkard place, i.e., between the man's legs just behind the scrotum. It may be quite difficult in one push from such an awkard place to drive enough fluid at a high enough pressure to cause rigidity of the portion of the cylinder contained in the pendulous section of the corpus cavernosum. Furthermore, the Burton et al invention does not have a sufficiently long rigid portion of the cylinder in the root of the corpus cavernosum during the erectile phase. Thus the device described by Burton et al may not provide sufficient stiffness and upward angle to give the penis a reasonably normal erectile state.

A copending patent application Ser. No. 476,931 filed by Fischell on Mar. 21, 1983, describes a penile erection device that is improved by eliminating a pump in the scrotum and by effecting the desired pumping action with a single thrust, but still requires two parts of the system to be implanted outside of the penis itself. The disadvantage of this design is that it requires more extensive surgery as compared with implanting the prothesis entirely within the corpus cavernosum. Similarly, a second copending application by Fischell, Ser. No. 526,893, filed Aug. 26, 1983, includes parts of the penile erection device that are outside of the penis itself, but this device includes a pressure-actuated mechanism that eliminates manual pumping to effect the erectile state.

The entire prior art cited above teaches away from the invention disclosed herein. The present invention is an inflatable penile prothesis entirely contained within the corpus cavernosum which allows fluid to be forced from a section within the root of the corpus cavernosum (i.e., within the body itself) into the pendulous portion of the corpus cavernosum thus allowing the erectile state to be physiologically normal by making it harder, longer, thicker, and at a rigidly held, upward angle without any pumping of fluid.

SUMMARY OF THE INVENTION

It is, therefore, highly desirable to provide a simple, safe, reliable, easy to operate and comparatively inconspicuous implantable device whereby the impotent male can achieve a penile erection that is physiologically normal; i.e., the device should cause the penis to become longer, thicker, harder, and stiffer, and to assume a generally upward angle. It is further desirable to have the penis return to a normal, flaccid condition at all times other than during sexual activity. Ideally, these two physiologically normal operating characteristics should be achievable promptly on command of the individual in whom the device is implanted. Furthermore, it is desirable to accomplish these objectives without requiring the implantable system to include any devices located outside of the corpus cavernosum.

To this end, one object of the present invention is to provide a means for readily causing the penis to achieve an erectile state which is physiologically equivalent to that of the normal male. Specifically, an object is to provide a device whereby the penis becomes longer, thicker, harder, stiffer, and attains a proper upward angle.

Another object of the invention is to provide a penile erection device having a readily achieved and physiologically normal flaccid state.

Yet a further object is to provide a penile erection device wherein the erectile state can be achieved rapidly by a single push of a valve located within a cylinder inside the corpus cavernosum without requiring pumping or manual squeezing of a reservoir containing the fluid that is to be displaced into the pendulous portion of the penile stiffener cylinder.

Another object is to provide a rigid reservoir within the root section of the corpus cavernosum containing a comparatively large fluid volume that is displaced into the pendulous portion of the stiffener cylinder to achieve the erectile state.

Still another object of the invention is to provide a device wherein the flaccid penile state can be achieved rapidly by a single push of a valve located within the corpus cavernosum at the base of the penis while simultaneously squeezing the penis with the other hand.

A further object of the invention is to provide an effective, fully implantable device wherein no part of the structure thereof is located outside of the corpora cavernosa.

Another object of the present invention is to provide a device wherein the reservoir is designed with a limited pressure capability so that neither of the two stiffener cylinders located in the corpora cavernosa can be overpressurized.

Yet a further object of the invention is to provide a fully implantable penile erection device including means for postoperatively adjusting the fluid level within the device, without surgical intervention, for adjusting the erectile and flaccid states.

Still another object of the invention is to provide a device which can be pre-assembled and pre-filled prior to surgical implantation so that the time required for the surgical implant is reduced.

Yet a further object of the present invention is to provide a manually actuated penile erection device that will not inadvertently return the penis to the flaccid state if the valve is accidentally actuated during sexual activity.

Yet another object of the present invention is to provide a penile erection device entirely contained within the corpora cavernosa which has a normally short, small and soft flaccid state and an erectile state which causes the penis to be harder, longer, stiffer, thicker, and at a proper upward angle.

Yet a further object of the present invention is to provide a penile prothesis that is operable from a source of electrical energy exterior to the body.

These and other objects of the invention, as well as many of the attendant advantages thereof, will become more readily apparent when reference is made to the following description, taken in conjunction with the accompanying drawings.

In the broad sense, an implantable apparatus for implantation at a selected location in a body according to the principles of the present invention comprises: at least one distensible member for implantation, each of the at least one distensible members forming an internal chamber, each of the at least one distensible members being distensible when their respective internal chambers are pressurized; pressure reservoir means; valve means coupling the respective internal chambers of each of the at least one distensible members to the pressure reservoir, each of the at least one distensible members not being in communication with the pressure reservoir when the valve means is at rest, each of the at least one distensible members and the pressure reservoir being in communication when the valve means is opened; a working fluid being disposed in the pressure reservoir means and being transferable between the internal chambers of each of the at least one distensible members and the pressure reservoir means; and fluid pressure generator means for pressurizing the working fluid in the pressure reservoir means when the valve means is at rest, opening of the valve means causing a transfer of the working fluid from the pressure reservoir means to the internal chambers of each of the at least one distensible members; all of the above being within the corpus cavernosum.

More specifically, an implantable apparatus for achieving penile erection in a human male according to the principles of the present invention comprises: at least one distensible cylinder for implantation in one of the corpora cavernosa of the penis of the human male, each of the at least one distensible cylinders having an internal chamber, each of the at least one distensible cylinders being distensible when the respective internal chambers are pressurized; pressure reservoir means; valve means coupling the respective internal chambers of each of the at least one distensible cylinders to the pressure reservoir, each of the at least one distensible cylinders not being in communication with the pressure reservoir when the valve means is at rest, each of the at least one distensible cylinders being in communication with the pressure reservoir when said valve means is opened; a working fluid being disposed in the pressure reservoir means and being transferable between the internal chambers of each of the at least one distensible cylinders and the pressure reservoir means; and fluid pressure generator means for pressurizing the working fluid in the pressure reservoir means, opening of the valve means causing a transfer of the working fluid from the pressure reservoir means to the internal chambers of each of the at least one distensible cylinders; all of the above being within the corpus cavernosum.

A method for permitting a human male to selectively achieve a penile erection in accordance with the principles of the present invention comprises the steps of: implanting in a human male at least one distensible cylinder in the corpus cavernosum of the penis, the distensible cylinder being distensible when supplied internally with a pressurized working fluid; and simultaneously implanting in the human male a pressure reservoir and pressure means for pressurizing a working fluid in the pressure reservoir, the distensible cylinder being in communication with the pressure reservoir through an also simultaneously implanted valve means; opening of the valve means causing flow of the working fluid from the pressure reservoir to the interiors of the distensible cylinders so as to cause a pressure increase therein and distension of the distensible cylinder; additionally the pressure reservoir, the working fluid and the valve means all being entirely contained within a single corpus cavernosum.

DETAILED DESCRIPTION OF THE DRAWINGS

Described herein is a penile erection device contained entirely within a corpus cavernosum of the penis. Although this is a workable arrangement, it is preferable, for effecting the most physiologically normal flaccid and erectile states, that a penile erection device be contained within each of the two corpora cavernosa. The device is powered by a vapor pressure driven fluid reservoir contained entirely within the root of the corpus cavernosum. The object of the invention is to drive the working fluid from the reservoir in the root into the pendulous section of the cylinder causing the penis to assume the erectile state without requiring pumping of the fluid and without requiring any section of the implanted device to be outside of the corpora cavernosa of the penis. A detailed description is given below.

Figures 1, 2:
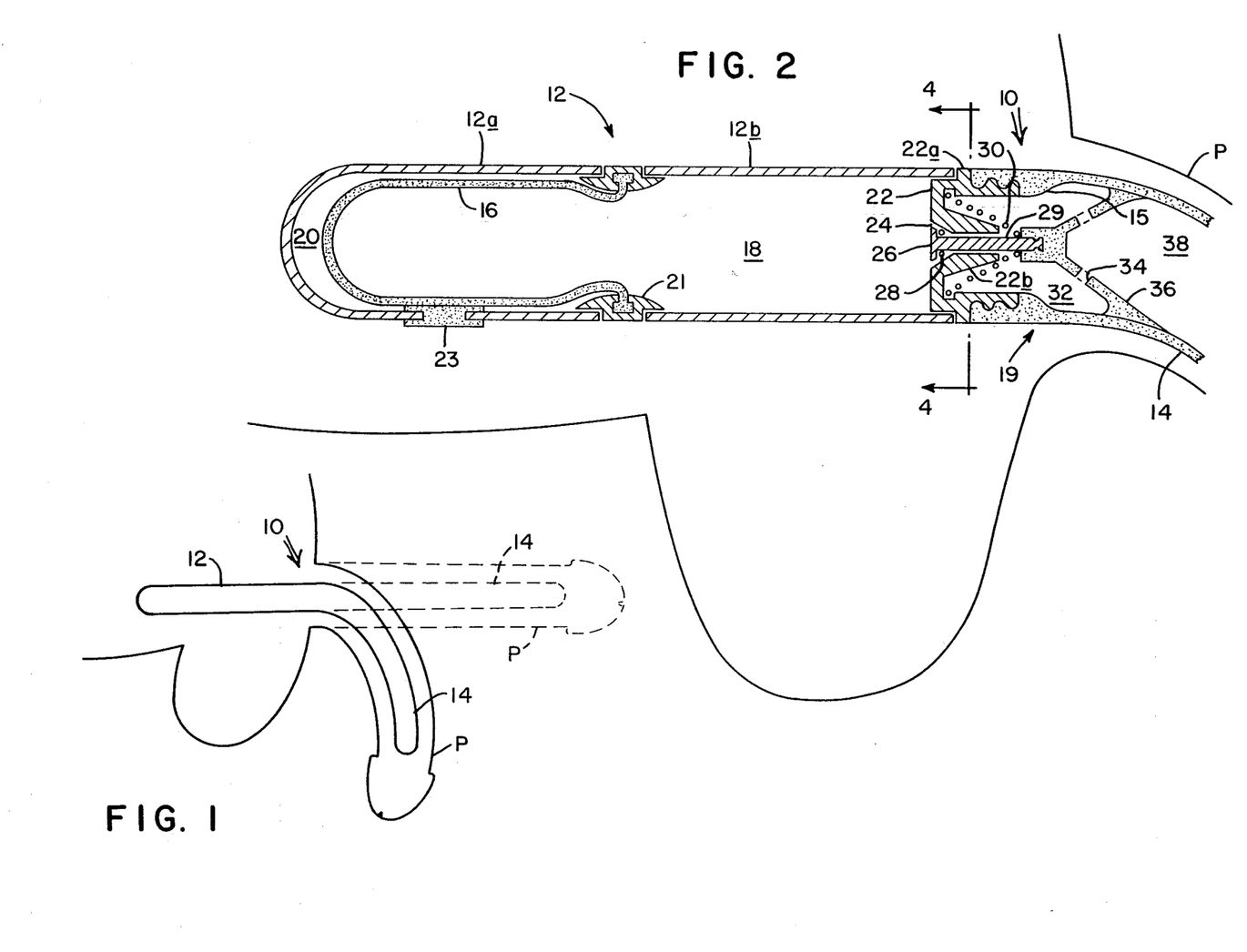
FIG. 1 is a side view of a fully implantable vapor pressure driven penile erection device, constructed in accordance with the principles of the subject invention, showing the penis in both the flaccid and the erectile states.
FIG. 2 is a cross-sectional view of a portion of the subject invention.

In FIG. 1 is shown the configuration of the cylinder 10 which is used to achieve either an erectile or flaccid state as desired by the man in whom this prothesis is implanted. The root section 12 is contained within the root of the corpus cavernosum; the pendulous section 14 is contained within the corpus cavernosum of the pendulous portion of the penis P. The cylinder 10 is shown both in the flaccid position in solid lines and in dotted lines for the erectile state of the penis P.

In FIG. 2 is shown a cross-sectional view of the cylinder 10 showing details of one preferred embodiment of the present invention. Contained within the root section 12 is a bladder diaphragm 16 made of an elastomer material such as bromobutyl rubber, polyurethane or silicone rubber. If, as shown in FIG. 2, the bladder 16 is in the position at the extreme left of the root section 12, then the root pressure reservoir chamber 18 will be filled with working fluid to its maximum extent. When the bladder 16 is driven to its extreme right position (not shown) as a result of the expansion of the liquid-vapor contained in the pressurant chamber 20, then the pendulous section 14 of the cylinder 10 will become stiffer, harder, longer and assume an upward angle because of an increased volume and pressure of the working fluid in the section 14. Thus the erectile state of the penis P is obtained.

The pressurant chamber 20 contains a liquid-vapor in equilibrium at body temperature at a pressure greater than atmospheric pressure. For example, the chamber 20 might contain a pressurant such as 2-methylbutane, which changes state between liquid and vapor as the fluid level within the chamber 20 is varied, but always maintains a constant pressure at constant temperature. At body temperature, the pressurant fluid maintains a pressure of approximately 6.3 pounds per square inch, gauge pressure (psig) (21.0 pounds per square inch, absolute (psia)) which is sufficient (but not excessive) for driving fluid into the penile stiffener cylinders. Thus, when the bladder 16 is in its position to the left as shown in FIG. 2, corresponding to the flaccid state of the penis, most of the pressurant fluid is in the liquid state and therefore the pressurant chamber 20 occupies very little volume. When the device is in the erectile state, most of the pressurant fluid is in the vapor state, thereby increasing the volume of the pressurant chamber 20 and moving the bladder 16 to the right, but always imparting a positive pressure to the working fluid contained in the reservoir chamber 18.

The pressure imparted to the working fluid depends upon three factors, namely (1) the type of pressurant used, (2) the temperature of the body (i.e., the temperature of the pressurant fluid), and (3) the stiffness of the bladder 16. Considering these three factors, one of ordinary skill in the art can select different bladders and pressurant fluid combinations suitable to produce the desired result within the principles and scope of the present invention.

Figure 3:
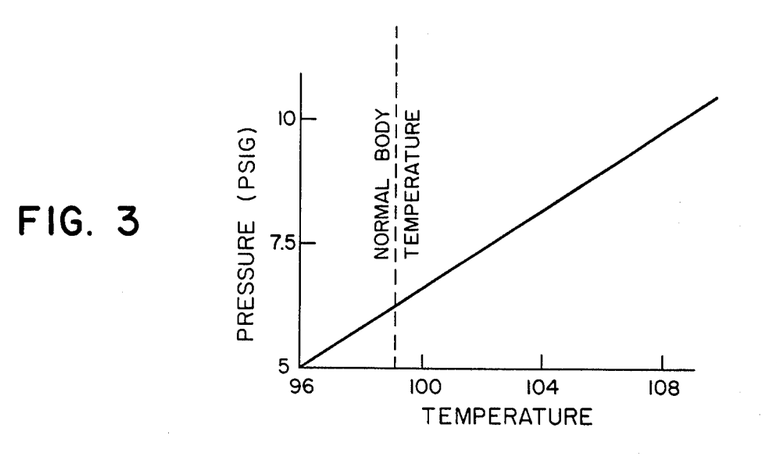
FIG. 3 graphically illustrates the pressure within the reservoir of the device as a function of body temperature.

FIG. 3 shows the curve of pressure versus temperature for the preferred pressurant fluid, 2-methylbutane. It should be understood, however, that any pressurant (such as a fluorocarbon) could be used that provides pressures in the range of 1 to 20 psig at normal body temperature.

Not illustrated in FIG. 3 is the possibility that the working fluid pressure is reduced by the pressure required from the pressurant for extension of the bladder. For a typical bladder, this effect is sufficiently small as to be negligible.

Returning now to FIG. 2, the bladder 16 is held in place near the center of the root section 12 by a ring 21 which is welded into the root section 12 so as to join together the two pieces of the outer shell, namely left root section shell 12a and right root section shell 12b. The ring both secures and seals the bladder 16 in place so that the bladder 16 will not leak, and so that the bladder 16 can assume any arbitrary position from the extreme left (as illustrated) to the extreme right of the root section 12 depending on how much working fluid is removed from the root reservoir chamber 18.

The left root section 12a, the right root section 12b and the ring 21 (as well as all other metal parts of the cylinder 10) preferrably are fabricated from CP titanium or from some alloy of titanium, or from any other metal that would not be damaged by the body's corrosive fluids or by the working fluid. Therefore, the root section 12 has a body that maintains a substantially constant volume. The working fluid might typically be a saline solution containing a radio-opaque dye, or a silicone fluid or any other fluid into which the pressurant could not readily dissolve. The pressurant, elastomer bladder material and the working fluid must be such that there is negligible diffusion of the pressurant into the working fluid.

There can be a sufficient excess of pressurant in the liquid state at its initial fill, combined with a sufficiently slow diffusion rate of the pressurant into the working fluid and from there into the body, so that there will be sufficient pressurant for many years (50 years for example). Still, there may be some diffusion of the pressurant through the bladder, and hence there is provided a pressurant refill septum 23 for recharging the pressurant as necessary by using a hypodermic syringe that can penetrate the body and enter the pressurant chamber 20 through the self-sealing septum 23. Such recharging would be accomplished only when the bladder 16 is displaced on the right side of the root section 12.

Located within the root section 12 is a valve arrangement 19 which attaches to the right root section shell 12b. One element of the valve arrangement 19 is a valve base 22 which is welded to section 12b to form a hermetic seal to contain the working fluid. Valve base 22 also forms a pressure seal with the flexible, pendulous section 14, forms a valve seat 24 for a valve poppet 26, holds a conically shaped compression spring 30, and forms an interior cylindrical surface to prevent the valve poppet 26 from cocking off its seated position.

Figure 4:
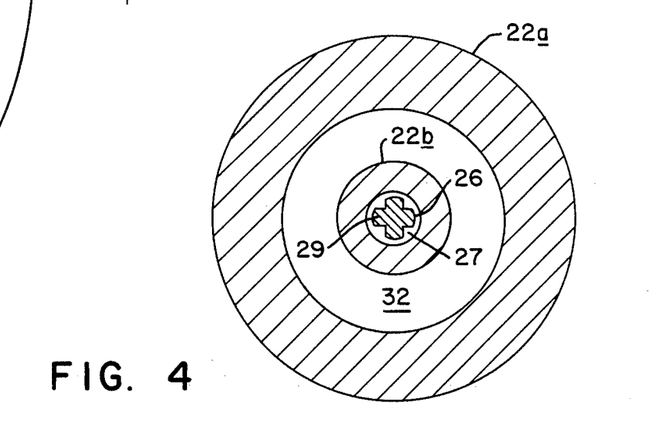
FIG. 4 is a cross-sectional view of the valve of the present invention taken substantially through the lines 4—4 of FIG. 2.

FIG. 4 is an enlarged sectional view of the valve 19 as shown at 4—4 in FIG. 2. The valve base 22 has an outer portion 22a and an inner portion 22b which are shown in both FIGS. 2 and 4. FIG. 4 shows that the cross section of the stem 29 of the valve poppet 26 takes the form of a cross as it passes through the inner cylinderical surface of the valve base inner portion 22b. This cross shape allows a fluid passageway 27 to be formed between stem 29 and the inner surface of portion 22b, while preventing cocking of the valve poppet 26 which might unseat an O-ring seal 28 (FIG. 2) from the valve seat 24. Between the valve base outer portion 22a and inner portion 22b is a fluid chamber 32 as seen in both FIGS. 2 and 4.

Returning now to FIG. 2, the conical compression spring 30 urges the valve poppet 26 to normally remain seated. Thus the pressure in the root reservoir 18 is normally maintained at pressurant pressure (6.3 psig for 2-methylbutane) irrespective of the position of the bladder 16. However, the pressure in the pendulous section 14 is maintained at approximately atmospheric pressure in the flaccid state but is allowed to go to a pressure as high as the pressurant pressure when the poppet 26 is forced open by squeezing the penis at its base as shown by the arrows "A" in FIG. 5. Pressuring at "A" causes the penis P to be deformed which, in turn, causes the pendulous section 14 to be deformed inwardly, deforming the elastomer conically shaped rib, or cone 36 and causing the cone to push the valve poppet 26 to the left in FIG. 5, i.e., to its open condition.

Figure 5:
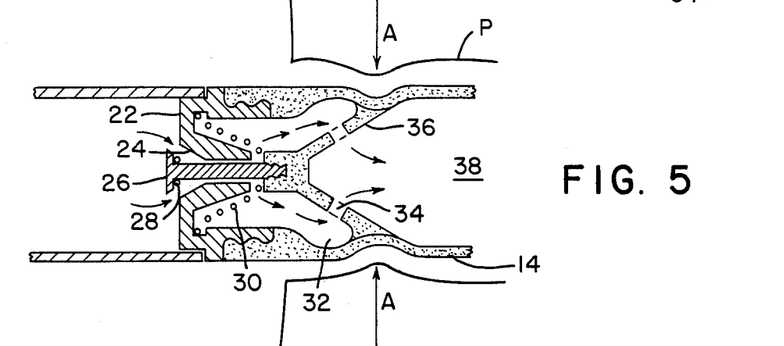
FIG. 5 illustrates the method for opening the valve within the root section of the implant to allow fluid to flow between the root reservoir chamber and the fluid chamber in the pendulous portion of the implant.

When the poppet 26 is pushed open, the O-ring 28 leaves the valve seat 24 thus causing flow of working fluid (due to the constant 6.3 psig pressure maintained in the pressurant chamber 20) from the root reservoir 18 toward the pendulous section chamber 38 as shown by the flow direction arrows of FIG. 5. Specifically, the fluid flows around the poppet 26, through the passageway 27, into chamber 32, then through four equally spaced holes 34 in the elastomer cone 36, and finally enters the pendulous section chamber 38. When this is accomplished, because of the increased pressure and volume of working fluid within the pendulous section 14, the penis becomes longer, thicker, harder, and assumes an upward angle, all of which constitutes the physiologically normal erectile state. When the erectile state is obtained, finger pressure is removed from "A" and the poppet 26 returns to its seated position due to the urging of the compressional spring 30. Even though the poppet 26 might inadvertently be opened during strenuous sexual activity, the pressure within the pendulous section 14 will be maintained and therefore the desired erectile state will not be affected.

The flaccid state is restored by using the thumb and index finger of one hand to again push at "A" (FIG. 5), hence opening the poppet 26, while squeezing the pendulous portion of the penis with the other hand. Thus the working fluid is forced to return to the root reservoir chamber 18 from the chamber 38 with the flow being opposite in direction to that shown by the flow arrows of FIG. 5.

The pendulous section 14 is made from a flexible elastomer such as silicone rubber or polyurethane. The section 14 is shrink fit onto the outer portion 22a of the valve base, and has a thick distal section 15. This section 15 of the elastomer serves four functions, namely: (1) it provides a strong mechanical joint onto section 22a, (2) it seals in the working fluid, (3) it provides stress relief at the point where the cylinder will bend when the penis is in its flaccid state, and (4) it serves as a self-sealing septum for post-surgically adding or deleting working fluid by means of a non-coring hypodermic needle that penetrates the base of the penis.

Figure 6:
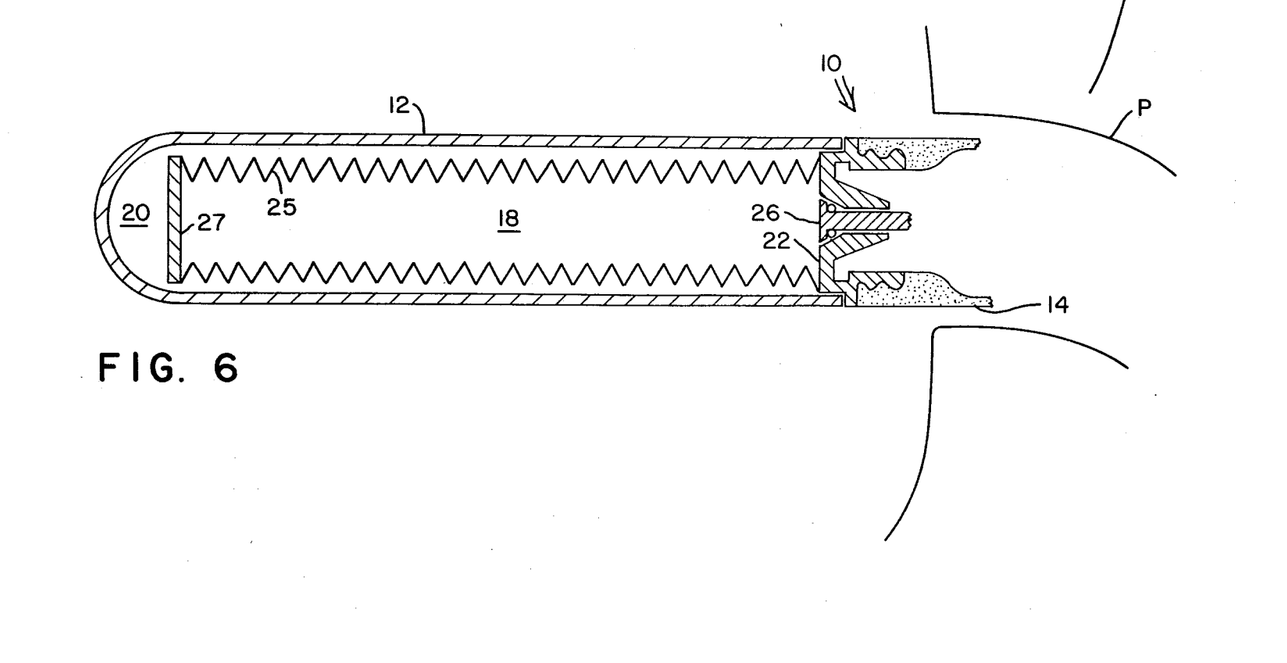
FIG. 6 shows an alternative embodiment of the present invention using an expandable bellows to separate the pressurant chamber from the working fluid chamber both being in the root section of the implant.

In FIG. 6 is shown an alternative embodiment of the present invention. Instead of using a bladder 16 as illustrated in FIG. 2, the design of FIG. 6 utilizes a closed bellows having convolutions 25 and an end plate 27. The convolutions 25 and end plate 27 are preferrably made of a metal such as titanium, although a plastic or elastomer material could be used. Exterior to the bellows and within a titanium outer shell 12 is the pressurant chamber 20 containing a pressurant such as 2-methylbutane. Within the bellows is a root reservoir chamber 18 containing the working fluid. When the valve poppet 26 is opened, the pressurant drives the end plate 27 to the right (not shown), therefore forcing the working fluid into the pendulous section 14 causing the erectile state of the penis. The flaccid state is obtained in a manner identical to the described above when reference was made to FIG. 2.

The advantage of using a metal to separate the pressurant from the working fluid is that there will be no diffusion of the pressurant through the metal into the working fluid and then into the body, which may be possible in the case of an elastomer bladder or a plastic or elastomer bellows.

Figure 7:
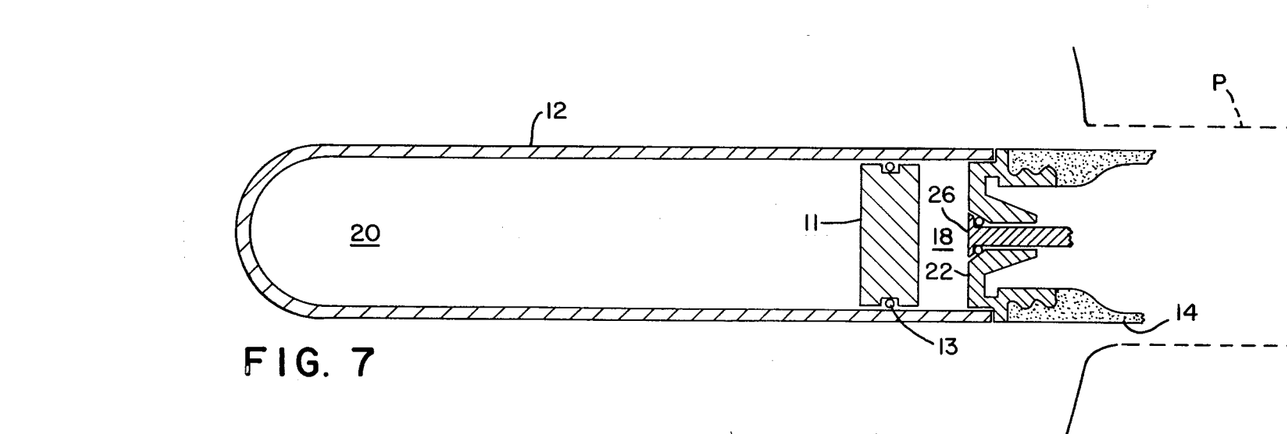
FIG. 7 shows another alternative embodiment of the present invention using a free piston within the root section to separate the pressurant from the working fluid.

FIG. 7 teaches a second alternative embodiment of the present invention. FIG. 7 shows a free piston 11 that uses an O-ring 13 in contact with the inner surface of the root section shell 12 to separate the pressurant chamber 20 from the working fluid in the root reservoir chamber 18. When the valve poppet 26 is opened as described above, the free piston 11 will move from the left of FIG. 7 to the right to be at the piston position as shown in FIG. 7. Thus the position of the free piston 11 as shown in FIG. 7 corresponds to the erectile state of the penis (as shown in dotted lines). In this condition, most of the pressurant will be in the vapor phase. The energy to restore the free piston 11 to the left of the root shell 12 is accomplished (as described above) by squeezing the penis with one hand while using the thumb and forefinger of the other hand to open the valve poppet 26.

Figure 8:
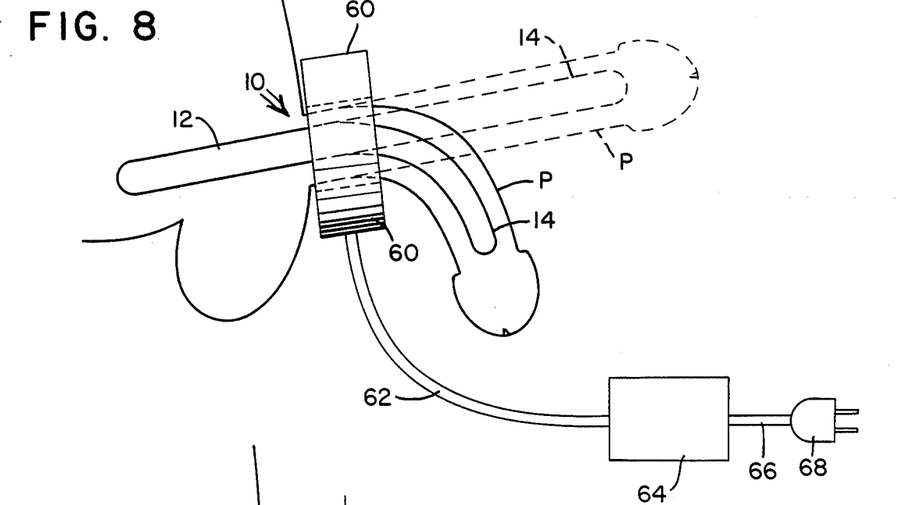
FIG. 8 shows the configuration of another alternative embodiment of the present invention using an external source of electrical energy to cause the erectile state.
Figures 9, 10:
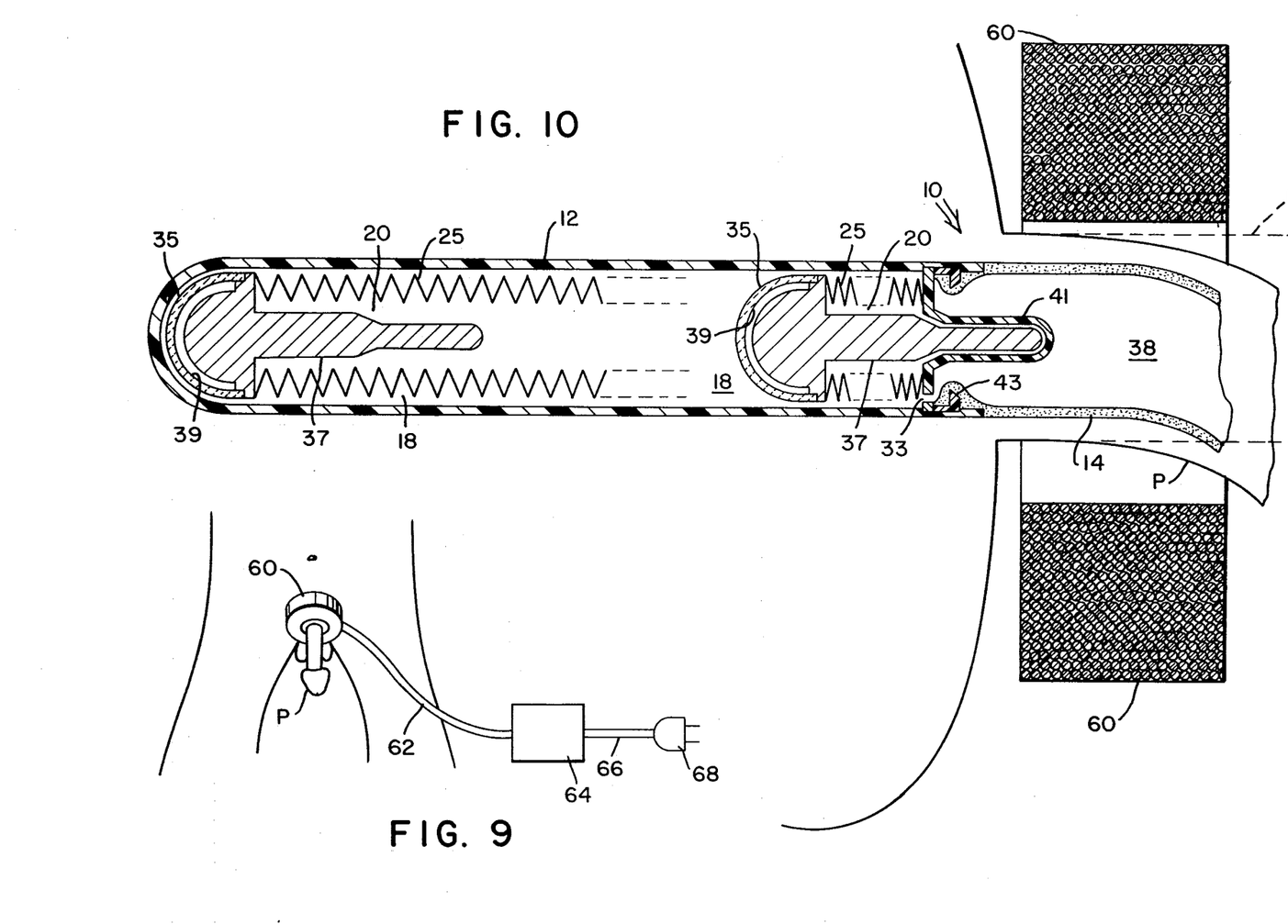
FIG. 9 is another view of the equipment for external powering of the penile implant.
FIG. 10 is a cross section of the externally powered penile implant.

The last embodiment described herein utilizes an external source of electrical energy to cause the erectile state to occur. With reference then to FIGS. 8 and 9, there is illustrated an embodiment using an external source of energy for causing the cylinder 10 to go from the flaccid state (as shown in solid lines) to the erectile state (as shown in dotted lines). The external energy source consists of a torroidal coil 60 that is placed around the base of the penis when it is desired to obtain the erectile state. The coil 60 is connected by electric wires 62 to a controller-transformer 64. External energy is provided by plugging into any 115 VAC electrical outlet by means of a plug 68 which then provides power to the controller-transformer 64 by means of the connecting wires 66.

The torroidal coil 60 is approximately 2 cm long, with an inside diameter of 3 cm and an outside diameter of 5 cm, and contains approximately 1,000 turns of #18 AWG copper wire wound as a solenoid. The magnetic field at the center of such a coil would have a peak value of approximately 5,000 Oersted when a peak current of 8 Amperes flows through the coil. The purpose of the controller-transformer 64 is to transform the line voltage down to that voltage which would provide an 8 Ampere peak current through the coil 60. Furthermore, the controller-transformer 64 preferably would have a control circuit which automatically would turn on the current for 30 seconds after the plug 68 is plugged in and the controller-transformer 64 is turned on, and then automatically would turn off for 10 minutes before it can be turned on again. The purpose of this function will be explained in connection with a description of the operation of the cylinder 10 of FIG. 10. The controller-transformer would also have an ON-OFF switch. Since any engineer of ordinary skill in the art could design such an external energy source, it is not deemed necessary for any further description.

In FIG. 10 is shown a cross-sectional view of the cylinder 10 of FIGS. 8 and 9, showing details of its construction, and also a simplified schematic view of the torroidal coil 60 showing its location relative to the base of the penis P.

The cylinder 10 has a plastic root section shell 12 which might be fabricated from a plastic material such as Nylon or Kelef. Contained within the shell 12 is a root fluid chamber 18 containing working fluid such as normal saline solution or an isotonic solution of a radio-opaque fluid. The principle of operation of this device is to decrease the volume of the root fluid chamber 18 so that the working fluid is driven through an orifice 33 into the pendulous section chamber 38 so as to cause the pendulous section 14 of the cylinder 10 to become harder, longer and thicker, i.e., to cause the penis P to assume a physiologically normal erectile state.

Contained within the root section shell 12 is an expandable bellows having convolutions 25 and a ceramic, hemispherical end plate 35. To the right in FIG. 10 is shown this bellows in its contracted state which provides the flaccid state as shown by the solid lines of the penis P. When the pressurant chamber 20 is expanded, the bellows convolutions 25 and the end plate 35 are driven to the left in FIG. 10, resulting in displacement of the working fluid from the root reservoir chamber 18, through the orifice 33 (which orifice 33 is part of base plate 41) into the chamber 38, causing the erectile state to occur as shown by the dotted lines of the penis P. The base plate 41 and the base plate holder ring 43 are preferentially fabricated from a plastic material so that they will not be heated by the alternating magnetic field.

Contained within the bellows is a heating element 37 which could be made from pure iron or a similar highly magnetic material which has a high eddy current and hysteresis energy loss in the presence of an alternating magnetic field. However, to avoid overheating of the iron heating element 37, the controller-transformer 10 remains on for only 30 seconds every 10 minutes. When element 37 is heated, the pressure in liquid-vapor chamber 20 is increased, thus driving element 37 to the left of FIG. 10. Such heating of the element 37 and movement of element 37 to the left, moves element 37 sufficiently far from the solenoid 60 so that even if the alternating magnetic field was maintained continuously, the heating effect would be negligible.

Figure 11:
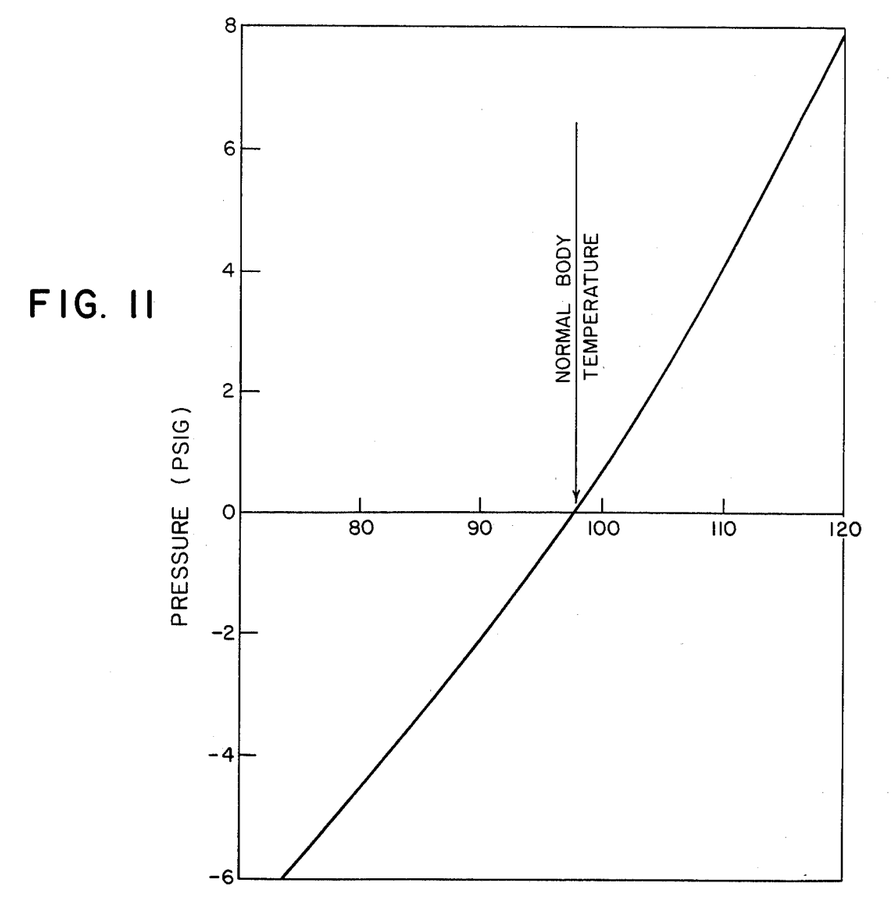
FIG. 11 shows the relationship of temperature and pressure for the pressurant Freon TMC.

The space within the bellows convolutions 25 and the iron heating element 37 is a pressurant liquid-vapor chamber 20 typically containing a fluorocarbon in equilibrium between its liquid and vapor phase. For example, the fluorocarbon might be Freon TMC whose pressure as a function of temperature is shown in FIG. 11. From FIG. 11 it can be seen that at normal body temperature, the pressure of the Freon is 0 psig or 14.7 psia. As the temperature is increased to 110° F. the pressure increases to +4 psig. Therefore, if the pressurant is heated above 98.6° F. by the action of the alternating magnetic field from the solenoid 60 acting on the heating element 37, the pressurant pressure will increase, the bellows will be displaced to the left (as shown in FIG. 10), the working fluid will be displaced out of the chamber 18, through the orifice 33, and into the pendulous fluid chamber 38 thus causing the erectile state to occur.

Figure 12:
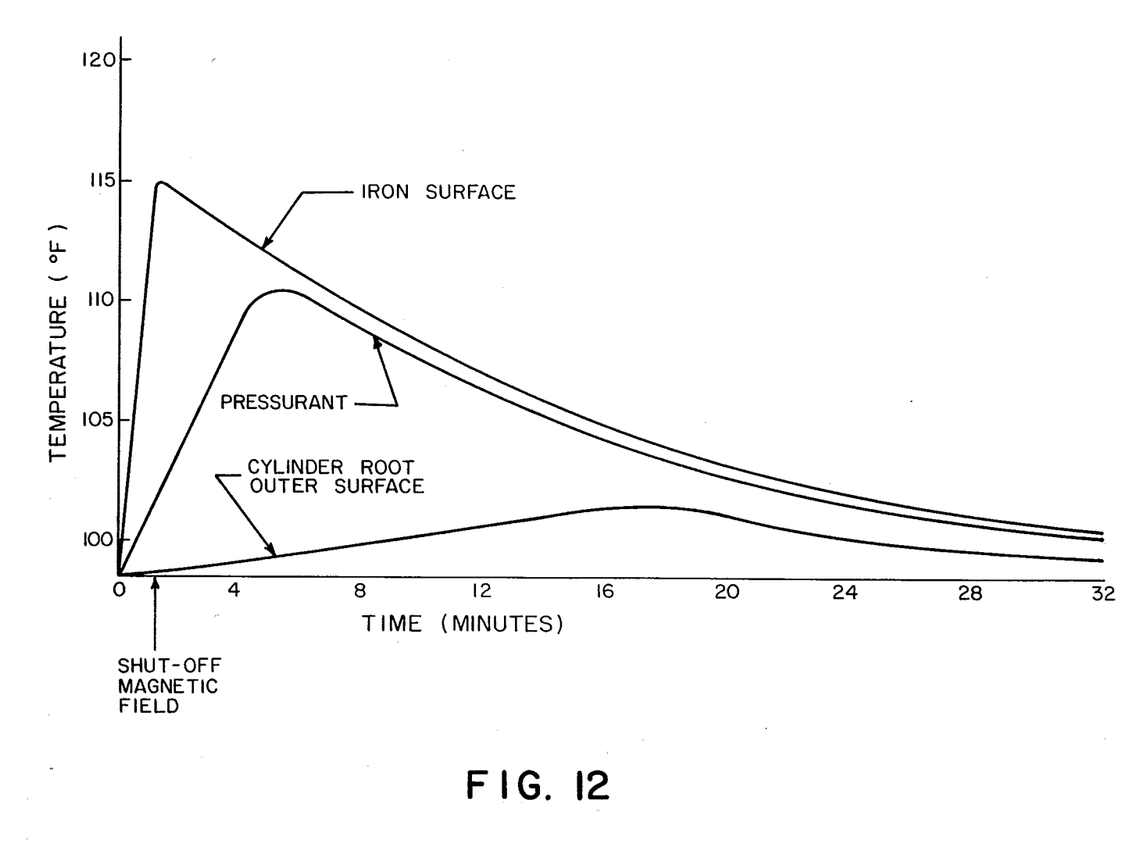
FIG. 12 shows the time history of temperature at several locations of the implant that is powered from an external source of electrical energy.

FIG. 12 shows typical temperatures of various portions of the system as a function of time after the alternating magnetic field from the solenoid 60 is applied to the heating element 37. It is important that the temperature of the pressurant reaches a high enough value so that an adequate working fluid pressure is achieved in order to provide a physiologically normal erectile state. Furthermore, it is desirable to maintain an adequate pressure for at least 20 minutes. If longer erectile times are required, either the solenoid could be reapplied or a valve arrangement at the distal end of the root shell 12 could be used to retain the pressure in the chamber 38 once it has been obtained. Such a valve system and method of its operation has been adequately described herein for the other embodiments of the present invention.

Another important aspect of the heated pressurant embodiment is that the temperature of the outer surface of the shell 12 should not exceed 104° F. A temperature of 104° F. is felt by the body to be comfortably warm. Substantially higher temperatures may be too hot. FIG. 12 shows an expected maximum temperature of the outer surface of the shell 12 to be less than 102° F.

The two conditions of maintaining a comparatively low temperature of the outer surface of the shell 12 and the comparatively long times for maintaining the pressurant at elevated temperatures are readily achievable because the heating element 37 has a high heat capacity, it takes a considerable loss of heat energy to change the pressurant from its vapor phase to its liquid phase, and there is no good heat transfer path from the pressurant into the body. In fact, the ceramic end plate 35 is a poor heat conductor and it encloses an evacuated space 39 between the interior surface of the end plate 35 and the external, hemispherical surface of the heating element 37 thus offering a high resistance heat path. Also, the pressurant itself is not a good head conductor and neither is the working fluid or the plastic shell 12. Thus the outer surface of shell 12 is maintained at an acceptably low temperature, and the pressurant maintains its comparatively high temperature (and hence pressure) for a long enough time to indulge in a reasonably extended sexual activity. When the pressurant cools below 100° F., the penis will return to a physiologically normal flaccid condition.

An alternating electromagnetic field could also be used to operate an electric motor to cause the working fluid to be pressurized. Likewise, once such an energy source is available, it could be used for returning the implant to the flaccid state. Thus the teachings of the present invention suggest the use of any external source of electrical energy for operating a penile implant to obtain either an erectile or flaccid state of the penis.

In all the embodiments described herein, the root section 12 of the cylinder 10 includes a flexible, distensible portion that is joined to the pendulous section 14. Thus during the flaccid state, the base of the penis will not feel unnaturally rigid and hard.

Various other modifications, adaptations and alternative designs are, of course, possible in light of the above teachings. Therefore, it should understood at this time that within the scope of the appended claims, the invention may be practiced otherwise than as specifically described herein.

What is claimed is:

1. A penile erection prosthesis for implantation totally within the corpus cavernosum of the penis of a human male, the prosthesis comprising: a rigid root section outer casing for implantation in the root of the corpus cavernosum; a flexible pendulous section outer casing for implantation in the pendulous portion of the penis; a sealed, variable volume pressurant chamber located in said rigid root section; a pressurant filling said pressurant chamber, said pressurant being capable of changing state at normal body temperature between liquid and vapor in dependence upon the volume of said pressurant chamber and maintaining a positive pressure in said pressurant chamber; a root reservoir chamber located in said rigid root section, one wall of which is moved in dependence upon the volume of said variable volume pressurant chamber; a pendulous section chamber located in said pendulous section outer casing, said pendulous section chamber being in fluid communication with said root reservoir chamber; a working fluid filling said root reservoir chamber and said pendulous section chamber; actuating means for bringing the penis from a flaccid to an erect state by increasing the volume of said pressurant chamber and thereby forcing said working fluid from said root reservoir chamber to said pendulous section chamber, said increasing of volume being accomplished by permitting at least a portion of said pressurant to change from its liquid state to its vapor state; and means for returning the penis to its flaccid state.

2. The device recited in claim 1, wherein said actuating means includes a manually operated valve intermediate said reservoir chamber and said pendulous chamber.

3. The device recited in claim 2, wherein said valve is a poppet valve.

4. The device recited in claim 3, and including a conical rib on which the stem of said poppet valve is mounted, whereby the application of manual pressure to said conical rib opens said poppet valve.

5. The device recited in claim 3, and including a conical spring for centering and maintaining said poppet valve in a normally closed position.

6. The device recited in claim 1, wherein said pressurant chamber is separated from said root reservoir chamber by a movable wall means.

7. The device recited in claim 6, wherein said wall means is an elastomeric baldder.

8. The device recited in claim 6, wherein said wall means is a bellows.

9. The device recited in claim 8, wherein said bellows is metallic.

10. The prosthesis recited in claim 6, wherein said wall means is a piston.

11. The device recited in claim 1, and further including a magnetic material located in proximity to said pressurant; and further including an external, electrically powered means for heating said magnetic material to thereby heat said pressurant and convert at least a portion of the same from its liquid state to its vapor state, and thus force said working fluid from said reservoir chamber to said pendulous chamber.

12. A penile erection device for implantation totally within the corpus cavernosum of the penis of a human male, the device comprising: a root section for implantation in the root of the corpus cavernosum, said root section having a body that maintains a substantially constant volume; a flexible pendulous section for implantation in the pendulous portion of the penis; a variable volume pressurant chamber; a pressurant filling said pressurant chamber, said pressurant being capable of changing state at normal body temperature between liquid and vapor and maintaining a positive pressure in said pressurant chamber; a reservoir chamber within said root section whose volume is dependent upon the volume of said variable volume pressurant chamber; a pendulous chamber located in said pendulous section, said pendulous chamber being in fluid communication with said reservoir chamber; a working fluid filling said reservoir chamber and said pendulous chamber; actuating means for bringing the penis from a flaccid to an erect state by increasing the volume of said pressurant chamber and thereby delivering said working fluid from said reservoir chamber to said pendulous chamber, said increasing of volume resulting from at least a portion of said pressurant changing from its liquid state to its vapor state; and means for returning the penis to its flaccid state.

13. The device recited in claim 12, wherein said pressurant has an equilibrium state at normal body temperature at a pressure above ambient.

14. The device recited in claim 13, wherein said actuating means includes a manually operated valve intermediate said reservoir chamber and said pendulous section chamber, whereby opening said valve permits the pressurant to vaporize and thereby increase the volume of said pressurant chamber to bring the penis to its erect state.

15. The device of claim 12, and further including means for adding pressurant to said pressurant chamber by means of a hypodermic syringe.

16. The device recited in claim 12, wherein said pendulous section is connected to said root section at the distal region of said pendulous section, said distal region being of increased wall thickness over the remaining region of said pendulous section.

17. The device recited in claim 16, wherein said distal region can be penetrated by a hypodermic syringe to add or remove a working fluid from the interior of said pendulous section.

18. A method for effecting a penile erection in an otherwise incapable human male by means of a device implanted totally within the corpus cavernosum of the penis, the method comprising the steps of implanting the root section of a prosthesis in the root of the corpus cavernosum; implanting a flexible pendulous section of said prosthesis in the pendulous portion of the penis; and manually operating said prosthesis so that a positive pressure internal pressurant contained within said root section in a body that maintains a substantially constant volume is permitted to change from a liquid state to a vapor state and thus expand, thereby moving a working fluid from a reservoir in said root section through a valve to the pendulous section and filling said pendulous section with said working fluid to thereby rigidify said pendulous section.

19. A penile erection device for implantation in a human male, the device comprising a flexible pendulous section for implantation in the pendulous portion of the penis; means for rigidifying said pendulous section and thus bringing the penis to an erect state by actuation through electrical means from a source external to the body; means for returning the penis to its flaccid state; a variable volume pressurant chamber filled with a pressurant; and a working fluid chamber filled with a working fluid; wherein said external electrical means serves to heat and expand said pressurant and thus to increase the volume of said pressurant chamber, thereby causing said working fluid to fill and to rigidify said pendulous section.

20. The device recited in claim 14, wherein opening said valve while simultaneously manually squeezing the penis causes vaporized pressurant to condense and thereby decrease the volume of said pressurant chamber to return the penis to its flaccid state.

21. The method of claim 18, but for effecting the flaccid state after the erect state has been obtained, and including the steps of manually opening a valve intermediate the reservoir and the pendulous section, and simultaneously manually squeezing the penis so that some pressurant vapor contained within said root section is forced to condense to the liquid state thereby removing fluid from said pendulous section and thereby causing said pendulous section to become flaccid.

* * * * *

UNITED STATES PATENT AND TRADEMARK OFFICE
CERTIFICATE OF CORRECTION

PATENT NO. : 4,572,168

DATED : Feb. 25, 1986

INVENTOR(S) : Robert E. FISCHELL

It is certified that error appears in the above-identified patent and that said Letters Patent is hereby corrected as shown below:

Column 14: Claim 2, line 1, change "1" to -- 12 --.

Claim 6, line 1, change "1" to -- 12 --.

Claim 10, line 1, change "prosthesis" to -- device --.

Claim 11, line 1, change "1" to -- 12 --.

Signed and Sealed this

Fifteenth Day of September, 1987

Attest:

DONALD J. QUIGG

Attesting Officer

Commissioner of Patents and Trademarks